US012121329B2

(12) United States Patent
Engman

(10) Patent No.: US 12,121,329 B2
(45) Date of Patent: Oct. 22, 2024

(54) WEARABLE VITAL SIGNS MONITOR WITH SELECTIVE SIGNAL ACQUISITION

(71) Applicant: West Affum Holdings DAC, Dublin (IE)

(72) Inventor: Zoie R. Engman, Kirkland, WA (US)

(73) Assignee: West Affum Holdings DAC, Grand Cayman (IE)

( * ) Notice: Subject to any disclaimer, the term of this patent is extended or adjusted under 35 U.S.C. 154(b) by 0 days.

(21) Appl. No.: 16/806,998

(22) Filed: Mar. 2, 2020

(65) Prior Publication Data

US 2020/0281479 A1    Sep. 10, 2020

Related U.S. Application Data

(60) Provisional application No. 62/815,914, filed on Mar. 8, 2019.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0024* (2013.01); *A61B 5/318* (2021.01); *A61B 5/6802* (2013.01); *A61B 5/6814* (2013.01); *A61B 5/6823* (2013.01); *A61B 5/6824* (2013.01); *A61B 5/6829* (2013.01);
(Continued)

(58) Field of Classification Search
CPC ... A61B 5/0205; A61B 5/6802; A61B 5/7275; A61B 5/6831; A61B 5/0024; A61B 5/6829; A61B 5/6814; A61B 5/6824; A61B 5/6823; A61B 5/742; A61B 5/1118;
(Continued)

(56) References Cited

U.S. PATENT DOCUMENTS 3,724,355 A    4/1973  Busch et al.
3,724,455 A    4/1973  Unger
(Continued)

FOREIGN PATENT DOCUMENTS

WO    9839061 A2    9/1998

OTHER PUBLICATIONS

"Elias Ebrahimzadeh, et al., A novel approach to predict sudden cardiac death (SCD) using nonlinear and time-frequency analyses from HRV signals", Feb. 4, 2014, PubMed (Year: 2014).*
(Continued)

*Primary Examiner* — Joseph M Dietrich
*Assistant Examiner* — Michael T. Holtzclaw
(74) *Attorney, Agent, or Firm* — Spectrum IP Law Group LLC

(57) ABSTRACT

In one example, a wearable vital sign monitor (WVSM) system comprises a support structure configured to be worn by a patient, a plurality of patient physiological sensors configured to be coupled to the patient when the patient is wearing the support structure, each patient physiological sensor configured to output a respective patient physiological signal, a memory, and, a processor communicatively coupled to the plurality of patient physiological sensors and configured to store in the memory measurements of patient physiological signals taken at selected times based on a categorization of the patient physiological signal.

13 Claims, 6 Drawing Sheets

SAMPLE COMPONENTS OF WEARABLE
CARDIOVERTER DEFIBRILLATOR (WCD) SYSTEM

(51) Int. Cl.
*A61B 5/024* (2006.01)
*A61B 5/11* (2006.01)
*A61B 5/318* (2021.01)
*A61N 1/372* (2006.01)
*A61N 1/39* (2006.01)

(52) U.S. Cl.
CPC .......... *A61B 5/6831* (2013.01); *A61B 5/7275* (2013.01); *A61B 5/742* (2013.01); *A61N 1/37247* (2013.01); *A61N 1/3904* (2017.08); *A61B 5/02405* (2013.01); *A61B 5/1118* (2013.01)

(58) Field of Classification Search
CPC .. A61B 5/02405; A61B 5/318; A61N 1/3904; A61N 1/37247
See application file for complete search history.

(56) References Cited

U.S. PATENT DOCUMENTS

| | | | |
|---|---|---|---|
| 4,583,524 A | 4/1986 | Hutchins | |
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,099,715 B2 | 8/2006 | Korzinov et al. | |
| 7,212,850 B2 | 5/2007 | Prystowsky et al. | |
| 7,559,902 B2 | 7/2009 | Ting et al. | |
| 7,587,237 B2 | 9/2009 | Korzinov et al. | |
| 7,865,238 B2 | 1/2011 | Brink | |
| 7,870,761 B2 | 1/2011 | Valentine et al. | |
| 7,907,996 B2 | 3/2011 | Prystowsky et al. | |
| 7,941,207 B2 | 5/2011 | Korzinov | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,579,516 B2 | 2/2017 | Kaib et al. | |
| 9,592,403 B2 | 3/2017 | Sullivan | |
| 11,013,409 B2 * | 5/2021 | Kaib | A61N 1/3968 |
| 11,083,906 B2 | 8/2021 | Foshee et al. | |
| 11,103,145 B1 * | 8/2021 | Sharma | A61B 5/6823 |
| 11,103,717 B2 | 8/2021 | Sullivan et al. | |
| 11,154,230 B2 | 10/2021 | Sullivan et al. | |
| 11,160,990 B1 | 11/2021 | Sullivan et al. | |
| 11,191,971 B2 | 12/2021 | Lu et al. | |
| 11,198,015 B2 | 12/2021 | Breske et al. | |
| 11,219,373 B2 * | 1/2022 | Eggers | A61B 5/681 |
| 11,324,405 B2 * | 5/2022 | Robinson | A61B 5/113 |
| 2002/0181680 A1 | 12/2002 | Linder et al. | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson et al. | |
| 2010/0298899 A1 * | 11/2010 | Donnelly | A61N 1/3904 607/6 |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0073486 A1 * | 3/2014 | Ahmed | A61B 5/02427 482/9 |
| 2014/0163663 A1 | 6/2014 | Poddar et al. | |
| 2014/0324112 A1 | 10/2014 | Macho et al. | |
| 2014/0378786 A1 * | 12/2014 | Hong | A61B 5/721 600/301 |
| 2014/0378812 A1 | 12/2014 | Saroka et al. | |
| 2015/0039053 A1 | 2/2015 | Kaib et al. | |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2018/0185662 A1 | 7/2018 | Foshee, Jr. et al. | |
| 2018/0242875 A1 * | 8/2018 | Volpe | A61B 5/363 |
| 2019/0110755 A1 * | 4/2019 | Capodilupo | A61B 5/7267 |
| 2019/0159696 A1 | 5/2019 | Meeker et al. | |
| 2019/0282178 A1 * | 9/2019 | Volosin | G16H 40/67 |
| 2019/0329054 A1 | 10/2019 | Breske et al. | |
| 2020/0027568 A1 | 1/2020 | Foshee, Jr. et al. | |
| 2020/0121251 A1 * | 4/2020 | Weber | A61B 5/6833 |
| 2020/0206518 A1 * | 7/2020 | Freeman | A61N 1/39046 |
| 2020/0230428 A1 | 7/2020 | Engman et al. | |
| 2020/0281479 A1 | 9/2020 | Engman | |
| 2021/0050111 A1 | 2/2021 | Engman et al. | |
| 2021/0370079 A9 | 12/2021 | Engman et al. | |

OTHER PUBLICATIONS

Heartstart MRx and XL AED Algorithm—Application Note, Jul. 2001, Edition 2 Philips Healthcare, USA.

(56) References Cited

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

\* cited by examiner

SAMPLE COMPONENTS OF WEARABLE
CARDIOVERTER DEFIBRILLATOR (WCD) SYSTEM

COMPONENTS OF SAMPLE WCD SYSTEM

WEARABLE VITAL SIGNS MONITOR WITH SELECTIVE SIGNAL ACQUISITION

CROSS-REFERENCE TO RELATED APPLICATIONS

The present application claims the benefit of U.S. Provisional Application No. 62/815,914 filed Mar. 8, 2019. Said Application No. 62/815,914 is hereby incorporated herein by reference in its entirety.

BACKGROUND

Wearable vital signs monitors (WVSMs) can provide benefits over non-wearable systems because such WVSMs can provide continuous 24/7 monitoring of key physiological signals. The accuracy of some physiologic signals, however, can be affected by the conditions under which they are sensed or collected. Furthermore, through study and analysis, it has been determined that acquisition of some physiological signals such as heart rate trend can be susceptible to noise or interference. Other signals such as resting heart rate can be difficult to measure unless the wearer has been sedentary for a certain period of time. Still other signals such as non-invasive blood pressure monitoring cannot be measured accurately unless the wearer is not moving to improve accuracy. Further still, some signals such as body weight cannot be measured with a WVSM and may involve using additional equipment such as a scale that is not a part of the core wearable system.

DESCRIPTION OF THE DRAWING FIGURES

Claimed subject matter is particularly pointed out and distinctly claimed in the concluding portion of the specification. However, such subject matter may be understood by reference to the following detailed description when read with the accompanying drawings in which:

Figure 1:
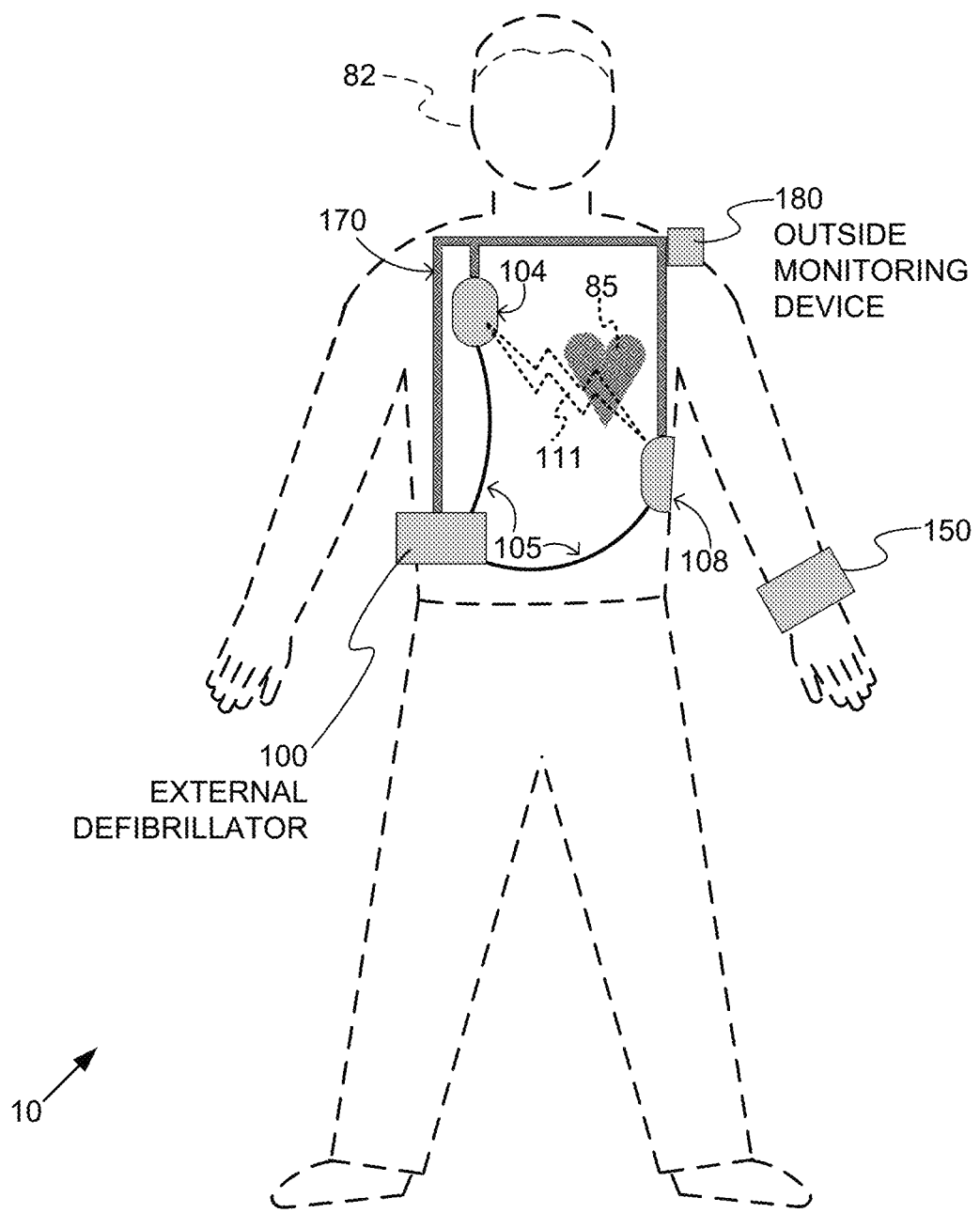
FIG. 1 is a diagram of components of a sample wearable cardioverter defibrillator (WCD) system incorporating a wearable vital sign monitor (WVSM) in accordance with one or more embodiments.

It will be appreciated that for simplicity and/or clarity of illustration, elements illustrated in the figures have not necessarily been drawn to scale. For example, the dimensions of some of the elements may be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. It will, however, be understood by those skilled in the art that claimed subject matter may be practiced without these specific details. In other instances, well-known methods, procedures, components and/or circuits have not been described in detail.

In the following description and/or claims, the terms coupled and/or connected, along with their derivatives, may be used. In particular embodiments, connected may be used to indicate that two or more elements are in direct physical and/or electrical contact with each other. Coupled may mean that two or more elements are in direct physical and/or electrical contact. However, coupled may also mean that two or more elements may not be in direct contact with each other, but yet may still cooperate and/or interact with each other. For example, "coupled" may mean that two or more elements do not contact each other but are indirectly joined together via another element or intermediate elements. Finally, the terms "on," "overlying," and "over" may be used in the following description and claims. "On," "overlying," and "over" may be used to indicate that two or more elements are in direct physical contact with each other. It should be noted, however, that "over" may also mean that two or more elements are not in direct contact with each other. For example, "over" may mean that one element is above another element but not contact each other and may have another element or elements in between the two elements. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect. In the following description and/or claims, the terms "comprise" and "include," along with their derivatives, may be used and are intended as synonyms for each other.

FIG. 1 is a diagram of components of a sample wearable cardioverter defibrillator (WCD) system incorporating a wearable vital sign monitor (WVSM) in accordance with one or more embodiments. A wearable cardioverter defibrillator (WCD) system 10 according to some embodiments can protect an ambulatory patient by electrically restarting his or her heart if needed. Such a WCD system 10 may have a number of components. These components can be provided separately as modules that can be interconnected, or can be combined with other components, and so on. In one or more embodiments, WCD system 10 can include a wearable vital systems monitor (WVSM) 150 that is capable of monitoring one or more physiological parameters of the patient 82 for example as one or more of the patient parameters collected by WCD system 10. WSVM 150 can come in a variety of form factors or support structures including, for example, a wrist band or watch, a chest band, an arm band, a head band, a leg band, or an ankle band. In other examples, WSVM 150 can be part of a support structure that comprises a cuff or similar device, or the support structure can comprise a vest, belt, or garment. In some embodiments, WSVM 150 can be part of WCD system 10, and in other embodiments, WVSM 150 can be completely separate from WCD system 10, and the scope of the disclosed subject matter is not limited in this respect.

In some embodiments, WSVM 150 can comprise a machine or computing platform comprising a processor and a memory coupled with the processor. The memory can include instructions thereon to configure the processor to perform any of the methods or operations described herein. In some examples, the methods or operations can be stored on a non-transitory machine readable or computer readable medium that, when the instructions are executed by the processor, configure the processor to perform any of the methods or operations described herein.

FIG. 1 depicts a patient 82. Patient 82 may also be referred to as a person and/or wearer, since the patient is wearing components of the WCD system 10. Patient 82 is ambulatory, which means that, while wearing the wearable portion of the WCD system 10, patient 82 can walk around and is not necessarily bed-ridden. While patient 82 may be considered to be also a "user" of the WCD system 10, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system 10 according to embodiments can be configured to defibrillate the patient 82 who is wearing the designated parts the WCD system 10. Defibrillating can be by the WCD system 10 delivering an electrical charge to the patient's body in the form of an electric shock. The electric shock can be delivered in one or more pulses.

FIG. 1 also depicts components of a WCD system 10 made according to embodiments. One such component is a support structure 170, or garment, that is wearable by ambulatory patient 82. Accordingly, support structure 170 can be configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170 and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037 which is incorporated herein by reference in its entirety. Support structure 170 can even be implemented as described for the support structure of U.S. application Ser. No. 15/120,655, published as US 2017/0056682 A1, which is incorporated herein by reference in its entirety. In such embodiments, the person skilled in the art will recognize that additional components of the WCD system 10 can be in the housing of a support structure instead of being attached externally to the support structure, for example as described in the US 2017/0056682 A1 document. There can be other examples.

FIG. 1 shows a sample external defibrillator 100. As described in more detail later in this document, some aspects of external defibrillator 100 include a housing and an energy storage module within the housing. As such, in the context of a WCD system 10, defibrillator 100 is sometimes called a main electronics module or a monitor. The energy storage module can be configured to store an electrical charge. Other components can cause at least some of the stored electrical charge to be discharged via electrodes through the patient to deliver one or more defibrillation shocks through the patient 82.

FIG. 1 also shows sample defibrillation electrodes 104 and/or 108, which are coupled to external defibrillator 100 via electrode leads 105. Defibrillation electrodes 104 and/or 108 can be configured to be worn by patient 82 in several ways. For instance, defibrillator 100 and defibrillation electrodes 104 and/or 108 can be coupled to support structure 170, directly or indirectly. In other words, support structure 170 can be configured to be worn by ambulatory patient 82 to maintain at least one of electrodes 104 and/or 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin but becomes biased that way upon sensing a condition that could merit intervention by the WCD system 10. In addition, many of the components of defibrillator 100 can be considered coupled to support structure 170 directly, or indirectly via at least one of defibrillation electrodes 104 and/or 108.

When defibrillation electrodes 104 and/or 108 make good electrical contact with the body of patient 82, defibrillator 100 can administer, via electrodes 104 and/or 108, a brief, strong electric pulse 111 through the body. Pulse 111 is also known as shock, defibrillation shock, therapy, electrotherapy, therapy shock, etc. Pulse 111 is intended to go through and restart heart 85 to save the life of patient 82. Pulse 111 can further include one or more pacing pulses of lesser magnitude to simply pace heart 85 if needed, and so on.

A typical defibrillator decides whether to defibrillate or not based on an electrocardiogram (ECG) signal of the patient. External defibrillator 100, however, may initiate defibrillation, or hold-off defibrillation, based on a variety of inputs, with the ECG signal merely being one of these inputs.

A WCD system 10 according to embodiments can obtain data from patient 82. For collecting such data, the WCD system 10 may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system 10, or a parameter of the environment, as will be described later in this document. In some embodiments, outside monitoring device 180 can comprise a hub or similar device through which connections and/or leads may be made of the various components of the WCD system 100. For example, at least some of the leads of external defibrillator 100 may be connected to and/or routed through the outside monitoring device 180 including, for example, one or more ECG leads, a right-leg drive (RLD) lead, leads connected to the defibrillation electrodes 104 and/or 108, and so on. In some embodiments, outside monitoring device 180 can include a controller or processor that is used to implement at least a portion of the shock/no-shock algorithm to determine whether a shock should or should not be applied to the patient 82, although the scope of the disclosed subject matter is not limited in this respect.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter. In other embodiments the input is qualitative, such as informing whether a threshold is crossed, and so on. Sometimes these inputs about patient 82 are also called physiological inputs and patient inputs. In embodiments, a sensor can be construed more broadly, as encompassing many individual sensors.

Optionally, device 180 can be physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system 10 may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system 10, in order to make its diagnoses more accurate, since patients' bodies differ from one another. Of course, such parameter values can be stored in a memory of the WCD system 10, and so on. Moreover, a programming interface can be made according to embodiments, which receives such measured values of baseline physiological parameters. Such a programming interface may input automatically in the WCD system 10 these, along with other data.

In one or more embodiments, WCD system 10 may include a wearable vital systems monitor (WVSM) 150 that is capable of monitoring one or more physiological parameters of the patient 82 as one or more of the patient parameters collected by WCD system 10. In some embodiments, WSVM 150 can be part of WCD system 10, and in other embodiments, WVSM 150 can be completely separate from WCD system 10, and the scope of the disclosed subject matter is not limited in this respect. In some examples, the WVSM 150 is capable of obtaining frequent physiological measurements while the patient 82 is wearing the WVSM 150 through the day and/or during the night when the patient 82 is sleeping.

The WVSM 150 can be provided in various types of form factors to be placed on the patient's body at various locations and/or to integrate with WCD system 10 in various ways. For example, in some embodiments, WVSM 150 can be worn on the wrist of the patient 82 or various other locations on the patient 82 such as on the arm, leg, ankle, chest, or back of the patient 82 depending on the provided form factor and/or technology utilized by the WVSM 150 to a physiological reading.

In some embodiments, WVSM 150 can be incorporated into an external device or accessory such as a smartphone. Such devices may come in various other form factors such as a patch, watch, earring, eyeglasses, ankle bracelet, and so on, wherein WVSM 150 can be unobtrusive.

In some embodiments, WVSM 150 can include a sensor built into the alert button or stop button of the WCD system 10 wherein the alert button or stop button is used by the patient 82 to stop an impending shock if the patient so desires. In such embodiments, the patient is already aware of the location of the alert button or stop button which would provide a simple and readily available device for the patient to use to take an appropriate measurement, for example a blood pressure or heart rate reading. For example, when WVSM 150 is in the alert button or stop button, the patient's blood pressure can be obtained whenever the patient 82 needs to abort a shock.

In one or more embodiments, WVSM 150 can include or otherwise comprise an optical pulse oximetry sensor and/or a methemoglobin sensor wherein optical NIBP sensor functionality can be implemented using a pulse oximetry or methemoglobin sensor. In other examples, WVSM 150 can comprise a cuff-less blood pressure monitor 150 can be incorporated in one or more of the ECG electrodes of the WCD system 10. Such a WVSM 150 can be an optical sensor or an electro-mechanical sensor such as described in "A CMOS-based Tactile Sensor for Continuous Blood Pressure Monitoring", Kirstein, Sedivy, et al., Proceedings of the Design, Automation and Test in Europe Conference and Exhibition, 1530-1591/05 (March 2005) which is incorporated herein by reference in its entirety.

In other embodiments, WVSM 150 can be adapted for use in proposed adhesive type defibrillators as disclosed in U.S. Pat. No. 8,024,037. For example, WVSM 150 can be disposed in one of the adhesive modules as shown in the '037 patent, or in an "appendage" or "flap" that extends from the module so that WVSM 150 can be positioned on an appropriate location on the patient. Embodiments of a WVSM 150 can include a wireless communication interface such as BLUETOOTH, near-field communication (NFC), Wi-Fi DIRECT, ZIGBEE, and so on, to transmit the physiological data to a module of the WCD system 10, to a personal communication device of the WCD system 10 for example as disclosed in U.S. Pat. No. 8,838,235, or to another remote device. Said U.S. Pat. No. 8,838,235 is incorporated herein by reference in its entirety. In some embodiments, a wired communication link can be used instead of a wireless communication link. For example, WVSM 150 can be implemented in an electrode that can be configured so that the blood pressure data is transmitted on a wire bundled with the wire or wires of the electrode sensors, or multiplexed on the same wire as the electrode data, and so on.

Figure 2:
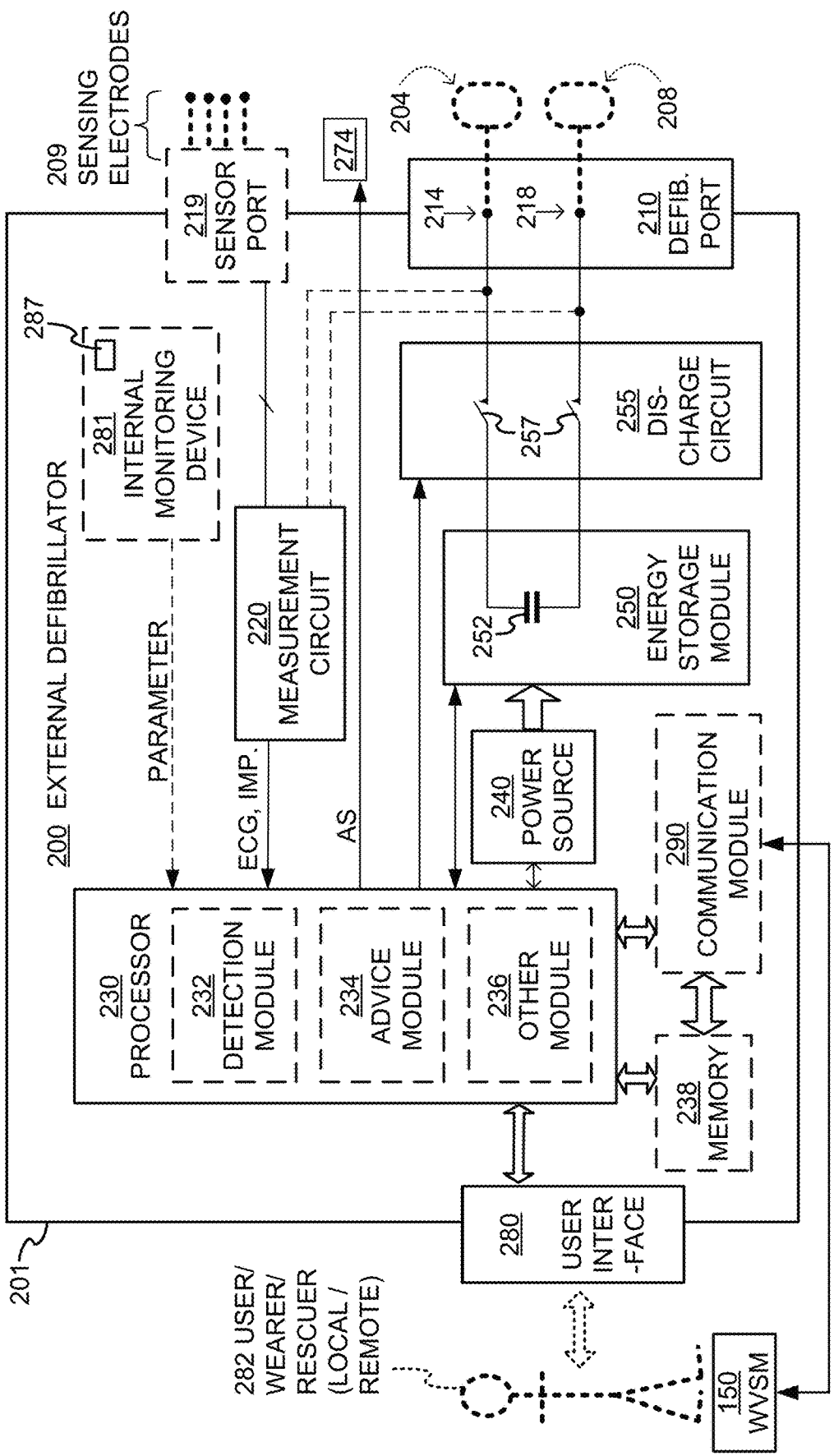
FIG. 2 is a diagram showing sample components of an external defibrillator, such as the one belonging in the system of FIG. 1, including a WVSM in accordance with one or more embodiments.

FIG. 2 is a diagram showing sample components of an external defibrillator, such as the one belonging in the system of FIG. 1, including a WVSM in accordance with one or more embodiments. Some components of WCD system 10 can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Alternatively, user 282 can be a local rescuer at the scene, such as a bystander who might offer assistance, or a trained person. Alternatively, user 282 might be a remotely located trained caregiver in communication with the WCD system 10.

User interface 280 can be made in a number of ways. User interface 280 may include output devices, which can be visual, audible or tactile, for communicating to a user 282 by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to user 282 acting as a rescuer for their resuscitation attempts, and so on. Another output device can be a speaker, which can be configured to issue voice prompts, beeps, loud alarm sounds and/or words to warn bystanders, etc.

User interface 280 further may include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock and may be referred to as a stop button in such embodiments.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors as also described elsewhere in this document.

Patient parameters may include patient physiological parameters. Patient physiological parameters may include, for example and without limitation, those physiological parameters that can be of any help in detecting by the WCD system 10 whether or not the patient is in need of a shock or other intervention or assistance. Patient physiological parameters may also optionally include the patient's medical history, event history, and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring device 180 and/or monitoring device 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In accordance with one or more embodiments, monitoring device 180 and/or monitoring device 281 may include WVSM 150 and may tangibly embody one or more embodiments of WVSM 150 or may operate in conjunction with WVSM 150, and the scope of the disclosed subject matter is not limited in this respect. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above; f) respiratory function, respiratory rate, etc.; g) motion, level of activity; and so on. Once a trend is detected, it can be stored and/or reported via a communication link, optionally along with a warning if warranted. From the report, a physician monitoring the progress of patient (user) 282 will know about a condition that is either not improving or deteriorating.

Patient state parameters include recorded aspects of patient (user) 282, such as motion, posture, whether they have spoken recently plus may be also what they said, and so on, plus optionally the history of these parameters. Alternatively, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether sudden cardiac arrest (SCA) is indeed taking place.

A WCD system 10 made according to embodiments may thus include a motion detector 287. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system 10 according to embodiments can be configured to detect a motion event. A motion event can be defined as is convenient, for example a change in motion from a baseline motion or rest, etc. In such cases, a sensed patient parameter can include motion.

System parameters of a WCD system 10 can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed or determined, if monitoring device 180 and/or monitoring device 281 includes a GPS location sensor as described above, and if it is presumed that the patient is wearing the WCD system 10.

Defibrillator 200 typically includes a defibrillation port 210, which can be a socket in housing 201. Defibrillation port 210 includes electrical node 214 and/or electrical node 218. Leads of defibrillation electrode 204 and/or defibrillation electrode 208, such as leads 105 of FIG. 1, can be plugged into defibrillation port 210 so as to make electrical contact with node 214 and node 218, respectively. It is also possible that defibrillation electrode 204 and/or defibrillation electrode 208 instead are connected continuously to defibrillation port 210. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if the leads make good electrical contact with the body of the patient and in particular with the skin of the patient. As with defibrillation electrodes 204 and/or 208, the support structure 170 can be configured to be worn by patient 282 so as to maintain sensing electrodes 209 on a body of patient (user) 282. For example, sensing electrodes 209 can be attached to the inside of support structure 170 for making good electrical contact with the patient, similarly with defibrillation electrodes 204 and/or 208.

Optionally a WCD system 10 according to embodiments also includes a fluid that can be deployed automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel so that it does not flow away after being deployed from the location it is released near the electrode. The fluid can be used for both defibrillation electrodes 204 and/or 208, and for sensing electrodes 209.

The fluid may be initially stored in a fluid reservoir, not shown in FIG. 2. Such a fluid reservoir can be coupled to the support structure 170. In addition, a WCD system 10 according to embodiments further includes a fluid deploying mechanism 274. Fluid deploying mechanism 274 can be configured to cause at least some of the fluid to be released from the reservoir, and be deployed near one or both of the patient locations to which electrodes 204 and/or 208 are configured to be attached to the patient. In some embodiments, fluid deploying mechanism 274 is activated prior to the electrical discharge responsive to receiving activation signal (AS) from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 optionally may obtain physiological signals through nodes 214 and/or 218 instead, when defibrillation electrodes 204 and/or 208 are attached to the patient. In these embodiments, the input reflects an ECG measurement. The patient parameter can be an ECG, which can be sensed as a voltage difference between electrodes 204 and 208. In addition, the patient parameter can be an impedance, which can be sensed between electrodes 204 and 208 and/or between the connections of sensor port 219 considered pairwise. Sensing the impedance can be useful for detecting, among other things, whether these electrodes 204 and/or 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory 238 can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful because VF typically results in sudden cardiac arrest (SCA). Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm (SAA). A Shock Advisory Algorithm can make a shock/no shock determination from one or more ECG signals that are captured according to embodiments, and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In good or ideal conditions, a very reliable shock/no shock determination can be made from a segment of the sensed ECG signal of the patient. In practice, however, the ECG signal is often corrupted by electrical noise, which can make it difficult to analyze. Too much noise sometimes causes an incorrect detection of a heart arrhythmia, resulting in a false alarm to the patient. Noisy ECG signals may be handled as described in U.S. application Ser. No. 16/037,990, filed on Jul. 17, 2018 and since published as US 2019/0030351 A1, and in U.S. application Ser. No. 16/038,007, filed on Jul. 17, 2018 and since published as US 2019/0030352 A1, both by the same applicant and incorporated herein by reference in their entireties.

Processor 230 can include additional modules, such as other module 236, for other functions. In addition, if internal monitoring device 281 is provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs and/or instructions for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230 and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200 or can be stored there after it is received by defibrillator 200.

Defibrillator 200 can optionally include a communication module 290, for establishing one or more wired and/or wireless communication links with other devices of other entities, such as a remote assistance center, Emergency Medical Services (EMS), and so on. The communication module 290 may include short range wireless communication circuitry for example in accordance with a BLUETOOTH or ZIGBEE standard, short or medium range wireless communication for example a W-Fi or wireless local area network (WLAN) in accordance with an Institute of Electrical and Electronics Engineers (IEEE) 802.11x standard, or a wireless wide area network (WWAN) in accordance with a Third Generation Partnership Project (3GPP) including a 3G, 4G, or 5G New Radio (NR) standard. The communication links can be used to transfer data and commands. The data may be patient data, event information, therapy attempted, cardiopulmonary resuscitation (CPR) performance, system data, environmental data, and so on. For example, communication module 290 may transmit wirelessly, e.g. on a daily basis, heart rate, respiratory rate, and other vital signs data to a server accessible over the internet, for instance as described in U.S. application Ser. No. 13/959,894 filed Aug. 6, 2012 and published as US 2014/0043149 A1 and which is incorporated herein by reference in its entirety. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc. Furthermore, in accordance with one or more embodiments, WVSM 150 can couple with communication module 290 of defibrillator 200 via a wired or wireless communication link. In some embodiments, WVSM 150 can couple with defibrillator 200 via outside monitoring device 180 of FIG. 1 acting as an intermediate device, connector, bus, router, switch, or hub, and the scope of the disclosed subject matter is not limited in this respect.

Defibrillator 200 also may include a power source 240. To enable portability of defibrillator 200, power source 240 typically includes a battery. Such a battery typically can be implemented as a battery pack, which can be rechargeable or not. Sometimes a combination of rechargeable and non-rechargeable battery packs is provided. Other embodiments of power source 240 can include an alternating current (AC) power override, for where AC power will be available, an energy-storing capacitor or bank of capacitors, and so on. Appropriate components may be included to provide for charging or replacing power source 240. In some embodiments, power source 240 is controlled and/or monitored by processor 230.

Defibrillator 200 additionally may include an energy storage module 250. Energy storage module 250 can be coupled to the support structure 170 of the WCD system 10, for example either directly or via the electrodes and their leads. Module 250 is where some electrical energy can be stored temporarily in the form of an electrical charge when preparing it for discharge to administer a shock. In some embodiments, module 250 can be charged from power source 240 to the desired amount of energy as controlled by processor 230. In typical implementations, module 250 includes a capacitor 252 which can be a single capacitor or a system or bank of capacitors, and so on. In some embodiments, energy storage module 250 includes a device that exhibits high power density such as an ultracapacitor. As described above, capacitor 252 can store the energy in the form of an electrical charge for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82 so as to deliver a shock 111 to patient 82.

For causing the discharge, defibrillator 200 can include a discharge circuit 255. When the decision is to shock, processor 230 can be configured to control discharge circuit 255 to discharge through the patient 82 at least some or all of the electrical charge stored in energy storage module 250. Discharging can be to nodes 214 and/or 218, and from there to defibrillation electrodes 204 and/or 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and by how long discharge circuit 255 is controlled to remain open. Defibrillator 200 optionally can include other components.

Figure 3:
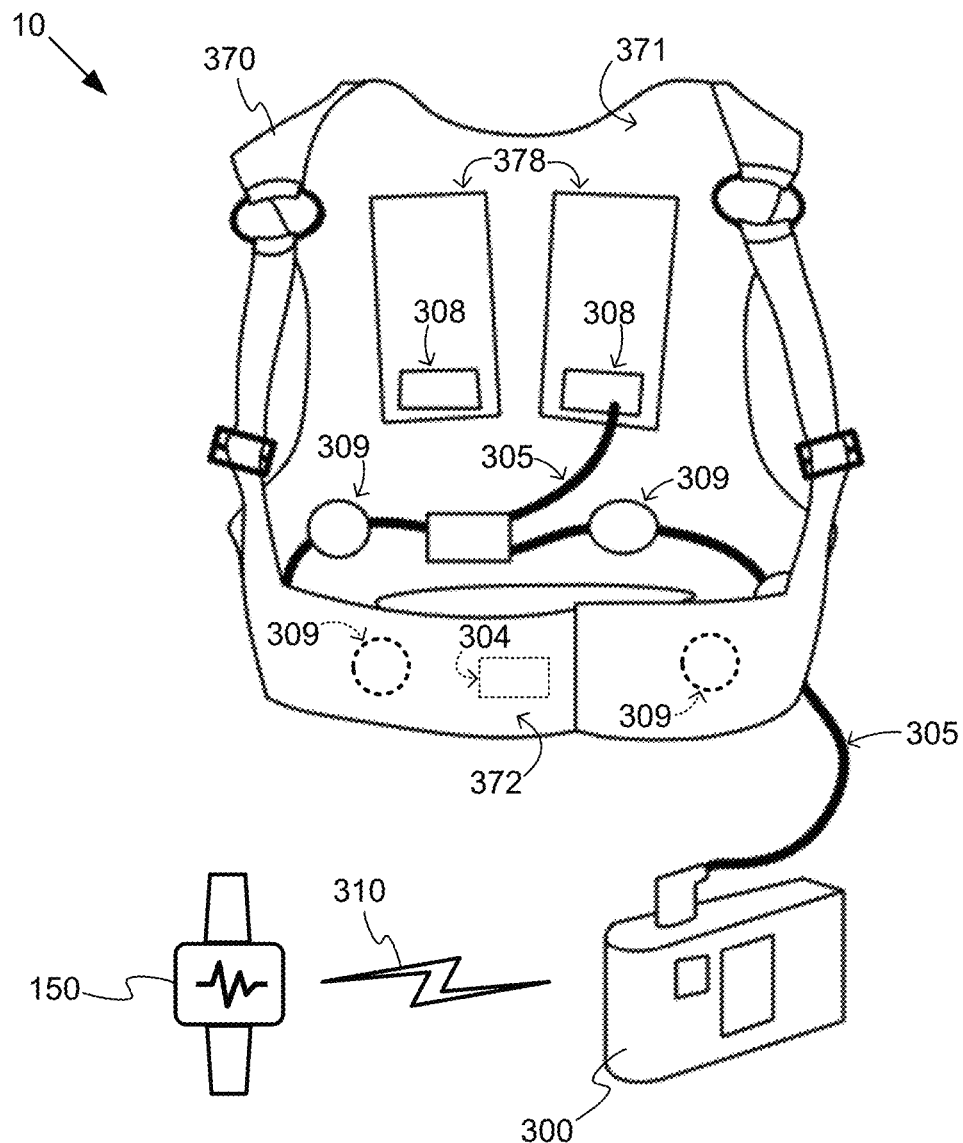
FIG. 3 is a diagram of sample embodiments of components of a WCD system and an WVSM monitor in accordance with one or more embodiments.

FIG. 3 is a diagram of sample embodiments of components of a WCD system and an WVSM monitor in accordance with one or more embodiments. A support structure 370 includes a vest-like wearable garment. Support structure 370 has a back side 371, and a front side 372 that closes in front of the chest of the patient. In some examples, WVSM 150 can operate as part of WCD system 10 as discussed in further detail below.

The WCD system 10 of FIG. 3 can include an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, and/or 309. Of those, electrodes 304 and 308 are defibrillation electrodes, and electrodes 309 are ECG sensing electrodes.

Support structure 370 is configured to be worn by the ambulatory patient to maintain electrodes 304, 308, and/or 309 on a body of the patient. Back defibrillation electrodes 308 can be maintained in pockets 378. The inside of pockets 378 can be made with loose netting, so that electrodes 308 can contact the back of the patient 82, especially with the help of the conductive fluid that has been deployed in such embodiments. In addition, sensing electrodes 309 are maintained in positions that surround the patient's torso, for sensing ECG signals and/or the impedance of the patient 82.

ECG signals in a WCD system 10 may include too much electrical noise to be useful. To ameliorate the problem, multiple ECG sensing electrodes 309 are provided, for presenting many options to processor 230. These options are different vectors for sensing the ECG signal, as described in more detail below.

In accordance with one or more embodiments, WVSM 150 can communicate with external defibrillator 300, for example via a wireless communication link 310 in some embodiments. In other embodiments, WVSM 150 150 also can communicate with external defibrillator 300 via a wired communication link, and the scope of the disclosed subject matter is not limited in this respect.

Figure 4:
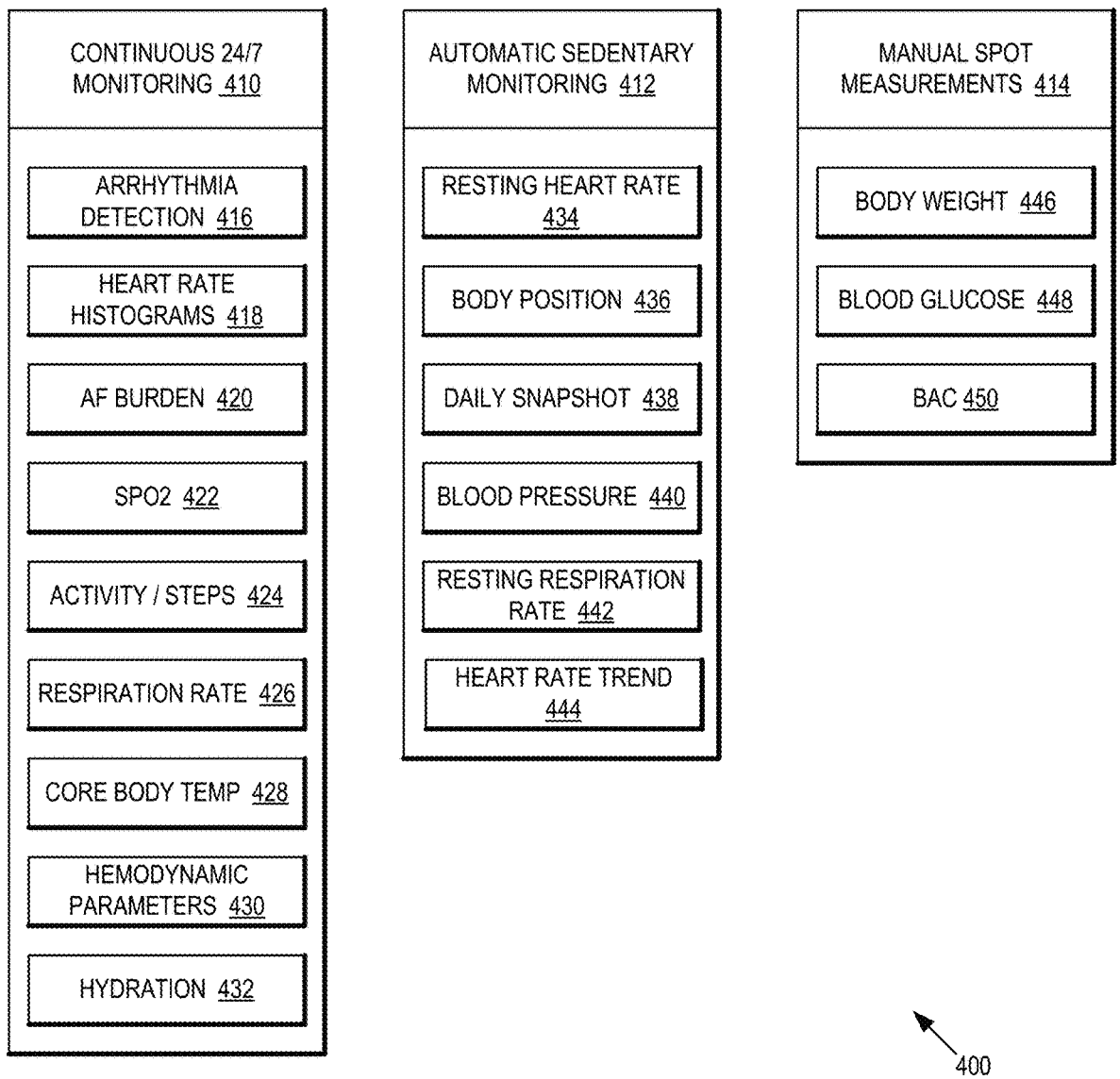
FIG. 4 is a diagram illustrating WVSM monitoring categories and the respective example physiological signals in each category in accordance with one or more embodiments.

FIG. 4 is a diagram illustrating WVSM monitoring categories and the respective example physiological signals in each category in accordance with one or more embodiments.

A WVSM 150 as described herein can be configured to acquire specific physiologic signals at optimal times to maximize the accuracy of the recorded data and enable a WVSM 150 to accurately monitor any physiologic signal that can be acquired non-invasively. In embodiments, any physiologic signal can be categorized into at least one of several different acquisition frequency categories. In one example categorization arrangement 400 as shown in FIG. 4, physiological signals can be assigned to one of following three categories. A first monitoring category 410 can comprise Continuous 24/7 Monitoring. Physiological signals in this category 410 are monitored continuously while the WVSM 150 is being worn by the patient 82 or user. Some examples of physiological parameters that can fall under the Continuous 24/7 Monitoring category 410 can include arrhythmia detection 416, heart rate histograms 418, atrial fibrillation (AF) burden 420, peripheral capillary oxygen saturation (SpO2) 422, activity and/or steps 424, respiration rate 426, core body temperature 428, hemodynamic parameters 430, or hydration 432, among others.

A second monitoring category 412 can comprise Automatic Sedentary Monitoring. Physiological signals in this category can be automatically monitored when the WVSM 150 determines that the patient 82 or user is sedentary or otherwise meets the criteria for a "resting" measurement. Some examples of physiological parameters that can fall under the Automatic Sedentary Monitoring category 412 can include resting heart rate 434, body position 436, daily snapshot 438, blood pressure 440, resting respiration rate 442, or heart rate trend 444, among others.

An example procedure for determining that the physiological signals that can fall within the Automatic Sedentary Monitoring category 412 to be acquired can include be any combination of the following. (a) Time-based via a one-time user input of "active" hours and "sedentary" hours; (b) Time-based via time of day (e.g. nighttime); (c) Sensed low activity or sleeping period using an accelerometer in the WVSM 150; (d) Triggered using analysis of the signals acquired by various sensors for the continuous 24/7 monitoring, for example the signals acquired by the continuous ECG sensors could be characterized as "not noisy", thereby triggering a sedentary recording of other physiologic signals; or (e) Triggered using sensed physiologic signals, for example a respiration rate below a certain threshold for a certain period of time could trigger a sedentary resting heart rate recording.

A third monitoring category 414 can comprise Manual Spot Measurements. Physiological signals in this category 414 can be monitored via manual intervention from the patient 82 or user, which can be triggered by user input to the WVSM 150, by physical attachment of an accessory component to acquire the signal, or by wireless communication with a compatible device. Some examples of physiological parameters that can fall under the Manual Spot Measurements category 414 can include body weight 446, blood glucose 448, or blood alcohol concentration (BAC) 450, among others.

In one example, as shown in FIG. 3, WVSM 150 can wirelessly communicate with WCD system 10 wherein WCD system 10 can obtain an ECG reading from the patient 82 and transmit the ECG reading to WSVM 150 for display, processing, or saving of the ECG reading. The ECG reading in can be obtained by the patient 82 initiating the WVSM 150 to obtain the ECG reading from the WCD system 10. In another example, WVSM 150 can be wirelessly coupled to a scale (not shown) and the weight reading from the scale can be wireless transmitted to the WVSM 150 for display, processing, or saving of the weight reading. Many other examples of Manual Spot Readings 414 can be utilized, and the scope of the disclosed subject matter is not limited in this respect.

In some embodiments, in addition to the physiological signals being sorted into frequency categories, the same physiological signal could be recorded continuously, while sedentary, and also manually, and then aggregated together to form an optimal, combined, or representative view of the physiologic signal. In some embodiments, the effect of noise or other artifacts on a continuous signal can be offset or factored out by the influence of a more accurate sedentary recording. An example of aggregating the same physiological signal taken at different times and/or in different categories is shown in and described with respect to FIG. 5, below.

Figure 5:
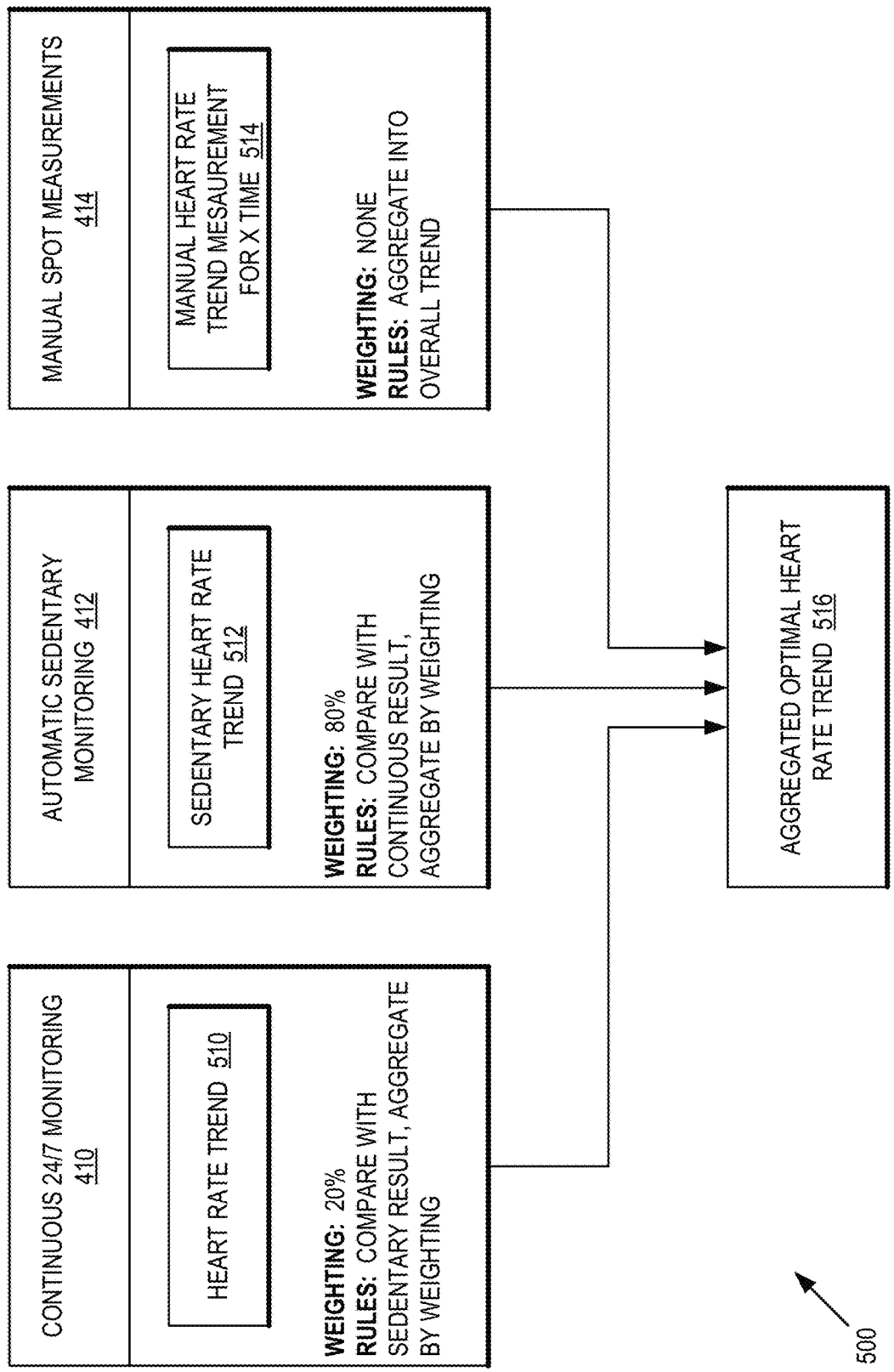
FIG. 5 is a diagram illustrating WVSM acquisition of a heart rate signal as an example in accordance with one or more embodiments.

FIG. 5 is a diagram illustrating WVSM acquisition of a heart rate signal as an example in accordance with one or more embodiments. In FIG. 5, aggregation process 500 can comprise obtaining a heart rate trend 510 using a Continuous 24/7 Monitoring process 410. In addition, a sedentary heart rate trend 512 can be obtained using an Automatic Sedentary Monitoring process 412. Furthermore, a manual heart rate trend measurement 514 for X amount of time can be obtained using a Manual Spot Measurements process 414. An aggregated optimal heart rate trend 516 can be obtained by combining the measurements from the categories, optionally applying weighting and/or rules to the measurements.

Table 1 below illustrates an example in which physiological signal aggregation and processing can be performed to generate optimal heart rate values that can be used to find a heart rate trend 516. In one example, the continuous heart rate trend measurement 510 can be recorded once per minute regardless of the presence of noise in a simple implementation. In some embodiments, when the WVSM 150 determines that it is time to acquire a sedentary heart rate, for example per the three categories described above, the sedentary heart rate trend measurement 512 value can be aggregated with the continuous measurement 510 result for that particular minute and weighted with more importance than the continuous measurement 510. For example, the sedentary heart rate trend measurement 512 can be weighted at 80 percent whereas the continuous heart rate trend measurement 510 can be weighted at 20 percent. Such an aggregation with weighting can result in a more accurate or representative aggregated heart rate trend, for example as shown in Table 1 below. Furthermore, a manual spot measurement 514 also can be aggregated into the overall trend, for example with no specific weighting to the measurement wherein the reading can stand alone. It is noted that these are merely examples of how measurements can be aggregated and/or weighted, and the scope of the disclosed subject matter is not limited in these respects.

TABLE 1

Example heart rate signal aggregation

| Time | Continuous Result | Sedentary Result | Aggregated Result |
|---|---|---|---|
| 2:00:00 | 65 bpm | None | 2:00 - 65 bpm |
| 2:01:00 | 150 bpm (noisy) | None | 2:01 - 75 bpm |
| 2:01:15 | None | 56 bpm | |
| 2:02:00 | 70 bpm | None | 2:02 - 70 bpm |
| 2:02:48 | | | +Manual - 82 bpm |

As shown in Table 1, at time 2:00:00 only a continuous heat rate measurement 510 was taken having a value of 65 beats per minute (bpm). The aggregated result for 2:00 is then 65 bpm. At time 2:01:00 a continuous result of 150 bpm was taken and flagged as noisy. For example, this higher reading is likely to be not entirely accurate. At time 2:01:15, a sedentary heart rate measurement 512 was obtained resulting in a value of 56 bpm. The sedentary result of 68 bpm can be weighted at 80% and combined with the continuous result weighted at 20% to result in an aggregated value at time 2:01 of (0.2) (150)+(0.8) (56)=75 bpm. At time 2:02:00 only a continuous heat rate measurement 510 was taken having a value of 70 bpm. The aggregated result for 2:02 is then 70 bpm. At time 2:02:48, only a single manual spot measurement was taken, with the resulting aggregated result of 82 bpm. It is noted that these are merely examples illustrating how measurements can be aggregated and/or weighted over multiple categories of measurement, and the scope of the disclosed subject matter is not limited in these respects.

In one or more example embodiments, aggregated measurements or a measurement trend, or both, can be presented to a user, patient 82, or a professional such as a doctor, physician assistant, nurse, technician, patient advocate, or other healthcare provider, and so on, for example on a display of the WVSM 150. In some examples, the aggregated measurements or measurement trend can be transmitted to a smartphone, tablet, computer, or similar computing device that is directly connected or wirelessly connected to the WVSM 150, or that is remotely connected the WVSM 150 via a network. Such remotely located devices and/or personnel use the aggregated measurements or measurement trend to provide assistance, medical care, or well-being advice, and so on, to the user or patient 82 based at least in part on the aggregated measurements or measurement trend. It should be noted these are merely examples of other devices and/or personnel that the aggregated measurements or trends can be transmitted to and monitored, and the scope of the claimed subject matter is not limited in these respects.

Figure 6:
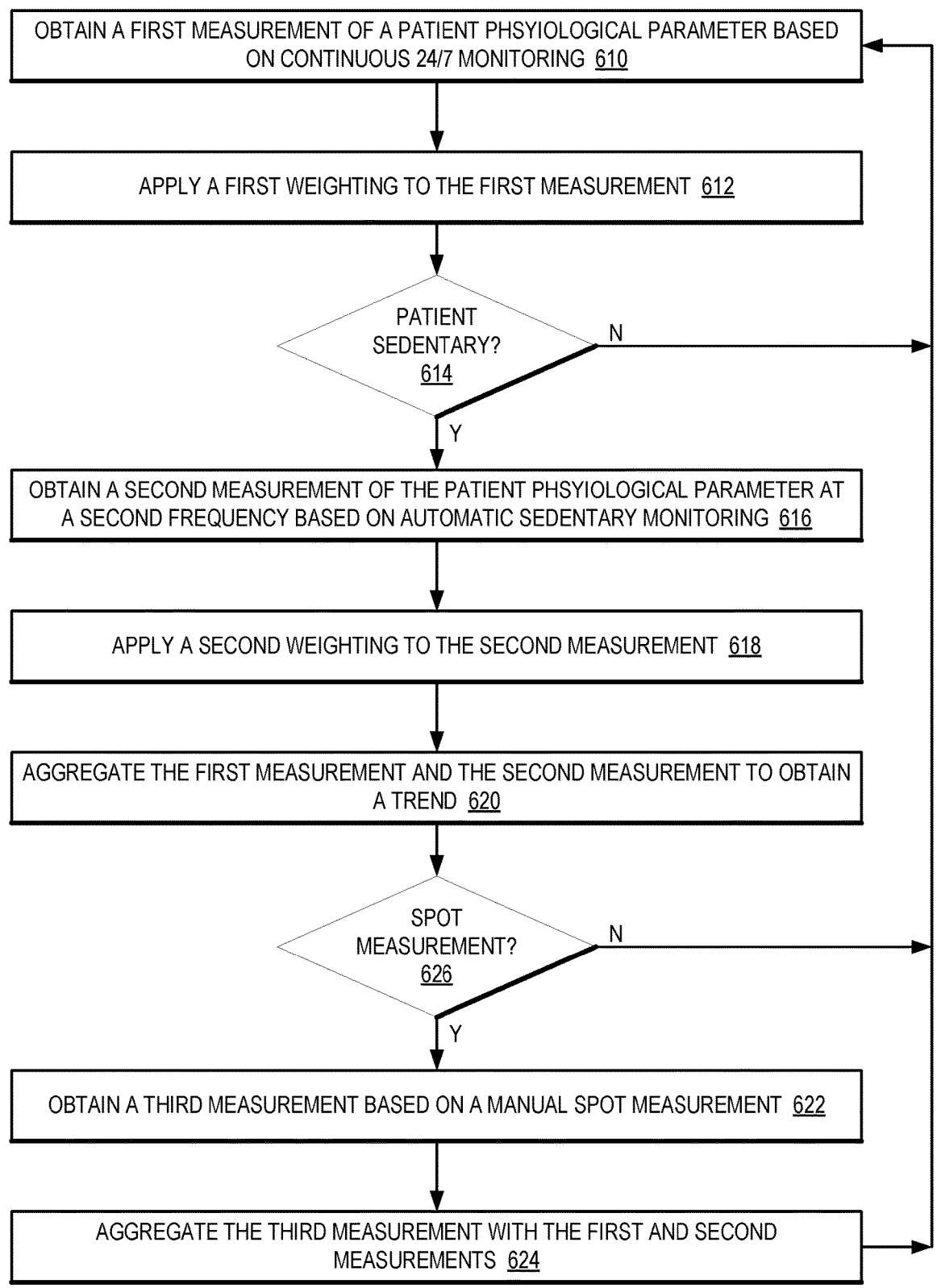
FIG. 6 is a flow diagram of a method of acquiring a patient physiological parameter using two or more categories of monitoring in accordance with one or more embodiments.

Referring now to FIG. 6, a flow diagram of a method of acquiring a patient physiological parameter using two or more categories of monitoring in accordance with one or more embodiments will be discussed. Although FIG. 6 shows one particular order and number of operations for method 600, various other orders or numbers of operations may be provided in alternative embodiments, and the scope of the disclosed subject matter is not limited in these respects. Method 600 illustrates one example of how physiological parameters can be obtained using different monitoring categories and then aggregated. At operation 610, a first measurement of a patient physiological parameter can be obtained based at a first frequency based on Continuous 24/7 Monitoring 410. In some examples, the first frequency can be continuous or can occur sufficiently often per a unit time to be considered continuous. Optionally, at operation 612, a first weighting can be applied to the first measurement. At operation 614, a determination can be made whether the patient 82 is sedentary. If not, then the Continuous 24/7 Monitoring 410 can continue at operation 610. If the patient 82 is stationary, then at operation 616 a second measurement of the patient physiological parameter can be obtained at a second frequency based on Automatic Sedentary Monitoring 412. For example, the frequency of such measurements can be obtained whenever the WSVM 150 detects that the patient 82 is sedentary or inactive. Optionally, a second weighting can be applied at operation 618 to the second measurement. The first and the second measurements can then be aggregated to obtain a trend at operation 620.

In some examples, a determination can be made at operation 626 whether a spot measurement should be made. If not, method 600 can continue at operation 610. If a spot measurement should be made, for example as triggered by the user or patient 82, or in response to some other device requesting the measurement such as a scale in response to the user or patient 82 stepping on the scale, then at operation 622 a third measurement can be obtained at a third frequency based on Manual Spot Measurement monitoring 414. Then, the third measurement can be aggregated with the first measurement, the second measurement, or both, at operation 624. In some examples, the third measurement can be obtained as a standalone measurement in the aggregation to be compared with other aggregated measurements, although the scope of the disclosed subject matter is not limited in this respect.

Although the claimed subject matter has been described with a certain degree of particularity, it should be recognized that elements thereof may be altered by persons skilled in the art without departing from the spirit and/or scope of claimed subject matter. It is believed that the subject matter pertaining to a wearable vital signs monitor with selective signal acquisition and many of its attendant utilities will be understood by the forgoing description, and it will be apparent that various changes may be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. A wearable vital sign monitor (WVSM) system comprising:
   a support structure configured to be worn by a patient;
   a plurality of patient physiological sensors configured to be coupled to the patient when the patient is wearing the support structure, each patient physiological sensor configured to output a respective patient physiological signal;
   a memory;
   a processor communicatively coupled to the plurality of patient physiological sensors and configured to store, in the memory, measurements of patient physiological signals taken at selected times based on a frequency categorization of the respective patient physiological signal; and
   a defibrillator configured to communicate with the processor;
   wherein the frequency categorization defines the selected times to measure a corresponding patient physiological signal and a frequency at which the measurements are obtained;
   wherein the processor causes a representation of the patient physiological signals to be displayed;
   wherein a first weight is applied to measurements obtained using a first frequency categorization of measurement, a second weight is applied to measurements obtained using a second frequency categorization of measurement, and a third weight is applied to measurements obtained using a third frequency categorization of measurement;
   wherein the first frequency categorization comprises continuous monitoring, the second frequency categorization comprises sedentary monitoring, and the third frequency categorization comprises manual spot measurements,
   wherein measurements in the second frequency categorization are triggered responsive to detection of sedentary activity for a predetermined period of time,
   wherein measurements in the third frequency categorization comprise body weight, blood glucose, and/or blood alcohol concentration (BAC) measurements;
   wherein the processor is configured to aggregate the measurements in the first frequency categorization, the measurements in the second frequency categorization and the measurements in the third frequency categorization to generate an aggregation of measurements, and to cause the defibrillator to apply a therapeutic shock to the patient based at least in part on the aggregated measurements; and
   wherein a magnitude of the first weight, a magnitude of the second weight, and a magnitude of the third weight are determined based on the frequency categorization to which the first weight, the second weight, and the third weight are applied for the aggregation of measurements.

2. The WVSM system of claim 1, wherein the defibrillator comprises one or more of the patient physiological sensors to obtain one or more of the measurements from the patient in one or more of the frequency categorizations, and to transmit the one or more of the measurements to the processor.

3. The WVSM system of claim 1, wherein the processor is configured to determine whether to apply the therapeutic shock to the patient based on a trend of measurements in one or more of the frequency categorizations.

4. The WVSM system of claim 1, wherein at least one of the plurality of patient physiological sensors is located external to the support structure, and the processor is configured to receive at least one of the patient physiological signals from the external sensor.

5. A method of operating a wearable vital signs monitor (WVSM), comprising:
   obtaining a first group of measurements of one or more patient physiological parameters using one or more patient physiological sensors, wherein the first measurement is obtained at a first frequency based on a first frequency category of monitoring;
   obtaining a second group of measurements of one or more of the patient physiological parameters using one or more of the patient physiological sensors, wherein the second measurement is obtained at a second frequency based on a second frequency category of monitoring;
   obtaining a third group of measurements of one or more of the patient physiological parameters using one or more of the patient physiological sensors, wherein the third measurement is obtained at a third frequency based on a third frequency category of monitoring;
   wherein the first frequency category, the second frequency category, and the third frequency category define selected times to measure a corresponding patient physiological parameter and a frequency at which the measurements are obtained;
   aggregating the first measurement, the second measurement, and the third measurement to obtain an aggregated trend for one or more of the patient physiological parameters;
   displaying the aggregated trend as a representation of the one or more of patient physiological parameters;
   wherein a first weight is applied to measurements obtained using the first frequency category of measurement, a second weight is applied to measurements obtained using the second frequency category of measurement, and a third weight is applied to measurements obtained using the third frequency category of measurement;
   wherein the first frequency category comprises continuous monitoring, the second frequency category comprises sedentary monitoring, and the third frequency category comprises manual spot measurements,
   wherein measurements in the second frequency category are triggered responsive to detection of sedentary activity for a predetermined period of time, and
   wherein measurements in the third frequency category comprise body weight, blood glucose, and/or blood alcohol concentration (BAC) measurements; and causing a defibrillator to apply a therapeutic shock to the patient based at least in part on the aggregated trend;

wherein a magnitude of the first weight, a magnitude of the second weight, and a magnitude of the third weight are determined based on the frequency categorization to which the first weight, the second weight, and the third weight are applied for the aggregation of measurements.

6. The method of claim 5, wherein one of the first measurement, the second measurement, or the third measurement is obtained from a device external to the WVSM.

7. The method of claim 5, wherein one of the first measurement, the second measurement, or the third measurement is obtained from a patient physiological sensor coupled with the defibrillator.

8. The method of claim 5, wherein one of the first measurement, the second measurement, or the third measurement is obtained with the patient physiological sensor and transmitted to the defibrillator.

9. A wearable vital sign monitor (WVSM) system, comprising:

a support structure to be worn by a patient;

a defibrillator configured to be coupled with the patient via the support structure;

one or more patient physiological sensors configured to be coupled to a patient to monitor one or more patient physiological parameters when the patient is wearing the support structure;

a local processor coupled with the one or more patient physiological sensors;

a memory to store measurements of the patient physiological parameters;

a display to display the patient physiological parameters;

wherein the local processor is configured to:

obtain a first measurement of the patient physiological parameters using a first patient physiological sensor, wherein the first measurement is obtained at a first frequency based on a first frequency category of monitoring;

obtain a second measurement of the patient physiological parameters using a second patient physiological sensor, wherein the second measurement is obtained at a second frequency based on a second frequency category of monitoring; and obtain a third measurement of the patient physiological parameters using a third patient physiological sensor, wherein the third measurement is obtained at a third frequency based on a third frequency category of monitoring;

wherein the first frequency category, the second frequency category, and the third frequency category define selected times to measure a corresponding patient physiological parameter and a frequency at which the measurements are obtained;

wherein the first frequency category comprises continuous monitoring, the second frequency category comprises sedentary monitoring, and the third frequency category comprises manual spot measurements, wherein measurements in the second frequency category are triggered responsive to detection of sedentary activity for a predetermined period of time, and wherein measurements in the third frequency category comprise body weight, blood glucose, and/or blood alcohol concentration (BAC) measurements; and a remote processor to receive the first measurement, the second measurement, and the third measurement from the local processor, wherein the remote processor is configured to:

aggregate the first measurement, the second measurement, and the third measurement to obtain an aggregated trend for the one or more patient physiological parameters;

store the aggregated trend in the memory; and display the aggregated trend as an aggregated representation of the one or more patient physiological parameters on the display;

wherein a first weight is applied to measurements obtained using a first frequency category of measurement, a second weight is applied to measurements obtained using a second frequency category of measurement, and a third weight is applied to measurements obtained using a third frequency category of measurement;

wherein the local processor is configured to receive the aggregated trend from the remote processor and to cause the defibrillator to apply a therapeutic shock to the patient based at least in part on the aggregated trend; and wherein a magnitude of the first weight, a magnitude of the second weight, and a magnitude of the third weight are determined based on the frequency categorization to which the first weight, the second weight, and the third weight are applied for the aggregation of measurements.

10. The WVSM system of claim 9, wherein the support structure comprises a wrist band, a chest band, an arm band, a head band, a leg band, or an ankle band.

11. The WVSM system of claim 9, wherein the support structure comprises a cuff.

12. The WVSM system of claim 9, wherein the support structure comprises a vest or a belt.

13. The WVSM system of claim 9, further comprising an additional patient physiological sensor located external to the support structure, and the processor is configured to receive at least one of the measurements from the external additional patient physiological sensor.

* * * * *